United States Patent [19]

Dalton et al.

[11] Patent Number: 4,594,324
[45] Date of Patent: Jun. 10, 1986

[54] MICROBIOLOGICAL PROCESS FOR OXIDIZING ORGANIC COMPOUNDS

[75] Inventors: Howard Dalton, Leamington Spa; John Colby, Burbage, both of England; David I. Stirling, Rutherglen, Scotland

[73] Assignee: National Research Development Corp., London, England

[21] Appl. No.: 453,825

[22] Filed: Dec. 28, 1982

Related U.S. Application Data

[63] Continuation of Ser. No. 296,361, Aug. 26, 1981, abandoned, which is a continuation of Ser. No. 157,169, Jun. 6, 1980, abandoned, which is a continuation of Ser. No. 921,610, Jul. 3, 1978, abandoned.

[30] Foreign Application Priority Data

Jul. 4, 1977 [GB] United Kingdom ............... 27886/77
May 25, 1978 [GB] United Kingdom ............... 27886/77

[51] Int. Cl.$^4$ ................. C12P 17/02; C12P 17/12; C12P 7/26; C12P 7/02; C12P 7/22; C12P 7/04; C12P 7/16; C12R 1/01; C12R 1/26
[52] U.S. Cl. ................................ 435/123; 435/122; 435/148; 435/155; 435/156; 435/157; 435/160; 435/822; 435/858
[58] Field of Search ................ 435/122, 123, 155, 156

[56] References Cited

U.S. PATENT DOCUMENTS 3,326,771 6/1967 Leavitt ................................ 435/136
3,846,245 11/1974 Kondis et al. ...................... 435/249

OTHER PUBLICATIONS

"Aspects of Ethane Metabolism in Methylobacteria", A. W. Thomson, Ph.D. thesis, Edinburgh University, 1974.
"A Methane-Dependent Coccus, with Notes on Classification and Nomenclature of Obligate, Methane-Utilizing Bacteria", J. W. Foster and Richard H. Davis, Journal of Bacteriology, May, 1966, vol. 91, No. 5, 1924–1931.
"Nitrogen-Fixation and Co-Oxidation of Ethylene by a Methane-Utilizing Bacterium", by J. A. M. de Bont and E. G. Mulder, Journal of General Microbiology (1974), 83, 113–121.
"An Improved Assay for Bacterial Methane Mono-Oxygenase: Some Properties of the Enzyme from *Methylomonas methanica*", by Colby, Dalton and Whittenbury, Biochem. J. (1975) 151, 459–462.
"The Different Types of Methane-Oxidizing Bacteria and Some of Their More Unusual Properties", by Whittenbury, Dalton, Eccleston and Reed, Extract from a book entitled Microbial Growth on $C_1$-Compounds, pp. 1–9 (1975).
"Some Properties of a Soluble Methane Mono-Oxygenase from *Methylococcus capsulatus* Strain Bath", by Colby and Dalton, Biochem. J. (1976) 157, 495–497.
Society for General Microbiology: proceedings-abstracts of papers delivered to the Jan. 1977 meeting held at Warwick Univ.
a. Abstract entitled "The Effect of Metabolisable Carbon Sources on the Physiology of the Methanotroph *Methylococcus capsulatus*", by Stanley, Dalton and Whittenbury.
b. Abstract entitled "Cometabolism by an Obligate Methanotrophic Bacterium, *Methylococcus capsulatus*", by Stirling and Dalton.
J. Gen. Microbil., 61, 205–218 (1970) paper by Whittenbury, Phillips and Wilkinson entitled "Enrichment, Isolation and Some Properties of Methane-Utilizing Bacteria".
Omori et al, Agr. Biol. Chem., 39 (9), 1775–1779 (1975).
Stanier et al, J. Gen. Microbiol., 43, 159, 160 and 204 (1966).
Whittenbury et al, J. Gen. Microbiol., 61, 205–218 (1970).

Primary Examiner—Alvin E. Tanenholtz
Attorney, Agent, or Firm—Oblon, Fisher, Spivak, McClelland & Maier

[57] ABSTRACT

A process in which a culture of a methane-oxidizing bacterium or an extract thereof containing a methane oxidizing system is used as oxidizing agent for the oxidation of a higher short-chain alkane, an alkene or a cyclic organic compound.

14 Claims, No Drawings

MICROBIOLOGICAL PROCESS FOR OXIDIZING ORGANIC COMPOUNDS

This application is a continuation of application Ser. No. 296,361, filed Aug. 26, 1981, now abandoned, which is a continuation of application Ser. No. 157,169, filed June 6, 1980, now abandoned, which is a continuation of application Ser. No. 921,610, filed July 3, 1978 now abandoned.

This invention relates to oxidation processes and in particular to microbial or enzymic oxidation of organic compounds.

Microorganisms capable of assimilating $C_1$ organic compounds as sources of carbon and energy have been known for many years, e.g. the *Bacillus methanicus* of Söhngen (Z. Bakteriol. Parasintenk. Abt II 15: 513–517). These organisms include methane oxidising bacteria, now generally identified by the prefix "Methylo" which are obligately dependent for growth on methane, methanol or dimethylether. It has been found, however, that these methane oxidising bacteria are also capable of oxidising, though not assimilating for growth, certain other organic substrates, such as ethers, alcohols and some short-chain alkanes. For example, it has been reported (Foster and Davis, Journal of Bacteriology May 1966, Vol. 91, No. 5, 1924–1931) that "resting cell" suspensions of the Texas strain of the bacterium *Methylococcus capsulatus* will oxidise certain primary alcohols and the short-chain alkanes, ethane and propane, though for these latter alkanes at rates considerably lower than those for methane oxidation.

It has been found that a much wider range of organic compounds is susceptible to oxidation by cultures and enzyme extracts of certain types of bacteria, than had hitherto been considered to be the case.

Accordingly the present invention comprises a process for the oxidation of a higher short-chain alkane, an alkene or a cyclic organic compound, in which a culture of a methane oxidising bacterium or a extract thereof containing a methane oxidising system is used as oxidising agent.

The term "higher short chain alkane" as herein used denotes an alkane having greater than three and less than nine carbon atoms, e.g. the straight chain alkanes: butane, pentane, hexane, heptane and octane, and the various branched-chain and other analogues thereof. The alkanes which may be oxidised by the present process may include substituted alkanes, though heavily substituted alkanes particularly those substituted with oxidation resistant groups may be oxidised less readily. For example, alkanes which are fully substituted at both terminal and penultimate carbon atoms by oxidation resistant substituents e.g. halogen substituents, may resist oxidation altogether. Oxidation of alkanes typically takes place predominantly at terminal and penultimate carbon atoms, generally to produce a mixture of 1 and 2 alcohols. The shorter chain alkanes e.g. butane and pentane and their analogues, may advantageously be oxidised at rates which compare favourably with the rate of oxidation of methane. Also, although the longer chain alkanes e.g. heptane, hexane, octane and their analogues, are oxidised at progressively lower rates, the fact of their oxidation is nevertheless a surprising and most unexpected finding.

In a preferred embodiment the present process is applicable to the oxidation of alkenes, including substituted alkenes, and alkenes having both terminal and internal double bonds. The process may be applied to alkenes in general and advantageously to lower alkenes in particular e.g. alkenes having a maximum carbon chain length of 10 or preferably 8 carbon atoms or less. Thus in a particular preferred embodiment, the present process is employed for oxidation of ethylene and butenes and especially propene. Alkenes having terminal double bonds are usually oxidised at the double bond generally to the corresponding 1,2-epoxide, and alkenes having internal double bonds may be oxidised both at the double bond and at terminal or penultimate carbon atoms normally to yield mixtures of the corresponding epoxides and terminal and penultimate alcohols. Also, internal alkenes of cis configuration may give rise inter alia to the production of ketones on oxidation.

Furthermore, and also unexpectedly, it has been found that the process of the invention may be applied to the oxidation of cyclic organic compounds. Cyclic compounds which may be oxidised include cycloalkanes, such as cyclohexane, unsaturated cyclic hydrocarbons including aromatic compounds e.g. benzene, toluene and styrene, and also heterocyclic compounds e.g. pyridine. Oxidation may occur either to the ring structure or, alternatively or in addition, to substituents attached to the ring. Thus, for example, it has been found that cyclohexane is oxidised to cyclohexanol and benzene is oxidised to phenol, whereas styrene is oxidised to styrene epoxide. On the other hand toluene is oxidised to a mixture of benzyl alcohol and cresol. Also oxidation of heterocyclic compounds may take place at hetero-atoms in the ring structure; for instance, pyridine has been found to be oxidised to pyridine N-oxide.

The bacteria which may be used for the process of the present invention are characteristically methane-oxidising bacteria, i.e. that class of $C_1$-assimilating bacteria which are obligately dependent for growth on methane or methanol, and in some cases are also capable of growth on dimethylether. Such bacteria are exemplified by the bacteria falling within the family group Methylomonadaceae as described in Bergey's Manual (1974), though it should be appreciated that the classification of these bacteria is by no means settled and is still open to considerable discussion in the bacteriological art. Thus suitable bacteria include bacteria of the genus Methylomonas, such as *M. methanica* e.g. the PM strain, and also bacteria of the genus Methylococcus, such as *M. capsulatus* e.g. the strain of *M. capsulatus* deposited with the American Type Culture collection as ATCC 19069. Suitable bacteria, however, also include bacteria of the genus *Methylomonas albus* e.g. the BG 8 strain, and *Methylomonas agile* e.g. the A 20 strain, and also the Bath strain of the organism *Methylococcus capsulatus* e.g. that deposited with the National Collection of Industrial Bacteria, Aberdeen, Scotland as NCIB 11132. Other methane-oxidising bacteria which are suitable for use in the present invention include bacteria of the genus Methylocystis such as the organism *Methylocystis parvum* e.g. the so called OBBP strain and bacteria of the genus Methylosinus such as the organism *Methylosinus trichosporium* e.g. the so called OB3b strain. The specific strains of organism given above as examples e.g. the PM strain, etc., are as described by Whittenbury et al (J. Gen. Microbiol 61 (1970) pages 205–218).

Any suitable strain of methane oxidising bacteria may be used for the process of the present invention. For example, suitable strains of *Methylococcus capsulatus* may be identified by the characteristics described in the paper by Foster and Davis (J. Bacteriol. May 1966. Vol. 91, No. 5 at page 1929) and the article by Whittenbury et al ("Microbial Growth on $C_1$ compounds" (1975) at page 7, ed. G. Terui, publ. The Society of Fermentation Technology, Tokyo). Thus, for example, the cells of *M. capsulatus* are typically non-motile Gram negative cocci, commonly found in diplococcoid arrangement and exhibiting marked encapsulation when viewed in India ink mounts; the organism which is an obligate aerobe capable of growth on methane and methanol in mineral salts medium is thermophilic and is able to grow at elevated temperatures e.g. ranging from about 30° to about 50° C. Strains of *M. capsulatus* together with Methylomonas sp. are typically distinguished from other methane oxidising bacteria by their incomplete TCA cycle which is 2-oxoglutarate dehydrogenase negative; *M. capsulatus* being further distinguished from Methylomonas sp. by containing an NAD specific isocitrate dehydrogenase, relatively low malate dehydrogenase activity and a G+C content of 62.5%. Examples of strains of *M. capsulatus* bacteria which may be used in the process of the invention include the Texas strain of *M. capsulatus*, such as that deposited as ATCC 19069, or preferably the Bath strain of *M. capsulatus*, such as that deposited as NCIB 11132.

Prior to use in the process of the invention, cultures of *M. capsulatus* may be maintained on a standard mineral containing culture medium provided the culture or atmosphere over the culture comprises a suitable growth substrate e.g. methane, and the culture is sub-cultured at relatively regular intervals. For instance, cultures of the Bath strain of *M. capsulatus* may be maintained on agar slopes surrounded by methane containing atmosphere, the cultures being sub-cultured regularly, preferably at least once a month.

The higher short chain alkanes, alkenes and cyclic compounds may be oxidised by contacting with living cells of the methane-oxidising bacteria, conveniently in the form of a suspension e.g. aqueous cell suspension. For example, a "resting cell" suspension of organism, previously grown on methane may be used, or preferably the oxidation system may be pulsed alternately with growth substrate and oxidation substrate. In a preferred embodiment the cells may be immobilised on or in a suitable support material, such as glass beads or a gel matrix which may be maintained as a packed or fluidised bed in a suitable contactor. In addition to the substrate for oxidation the presence of an additional compound such as methane, methanol or preferably formaldehyde or formate may be required to supply reducing power for the methane-oxidising system.

The use of whole cells is particularly suitable for the oxidation of the lower molecular weight and/or more lipophilic substrates which may be advantageously absorbed through the cell membrane. In relation to the use of thermophilic methane-oxidising bacteria such as *M. capsulatus* the use of whole cells is particularly advantageous in view of the high growth temperatures e.g. an optimum growth temperature of 45° C. for *M. capsulatus* (Bath), which may be tolerated by the organisms, thus conveniently diminishing cooling requirements.

As an alternative to the use of whole cells, appropriate enzyme extracts of methane-oxidising bacteria may be used, and may be either membrane associated or soluble extracts. Preferably soluble enzyme extracts, such as those obtained from the Bath strain of *M. capsulatus*, for instance by centrifugation of crude cell extracts, may be employed. Substrates may be oxidised by direct interaction with solution or suspension of extracts, or more preferably the extracts are first immobilised by attachment to or within a suitable solid phase material, such as glass, cellulose or a synthetic polymeric material, which is contacted with the substrate. The use of extracts is generally applicable to the oxidation of all substrates included within the scope of the invention though, it will be appreciated, however, that when extracts are used co-factors e.g. NADH, are usually required for oxidation to proceed. Thus processes according to the invention employing enzyme extracts typically comprise as an essential feature the supply, or preferably the regeneration, of co-factors or other biochemical species required to drive the enzymatic reaction. Any suitable method or means may be employed fo regeneration of these required biochemical species. For instance, with crude enzyme preparations, formate or formaldehyde, or other suitable electron donor material, together with a catalytic amount of NAD+ may be used to regenerate NADH required to drive the enzymatic reaction. Catalytic quantities of other required biochemical species may be regenerated similarly.

For a given substrate the rate of oxidation and products obtained may vary having regard to the type of oxidising agent used e.g. enzyme extract or whole cells, the species of organism and conditions employed during the oxidation process, and the rate of oxidation and products may be optimised as required. Optimum organisms and conditions may be determined by simple experiments which will be apparent to workers skilled in the art, e.g. similar to those described hereinafter in the specific examples. For example, in the oxidation of propene using whole organism of various methane-oxidising bacteria, organisms of the genus Methylomonas, especially *M. Albus*, have been found to exhibit particularly desirable specific activities for oxidation of the propene to 1,2-epoxypropane.

The invention is further illustrated in the following non-limiting examples which relate to growth of bacteria and oxidation of higher short chain alkanes, alkenes and cyclic organic compounds.

EXAMPLE 1

Growth of Bacteria and Preparation of Soluble Extracts

*Methylococcus capsulatus* (Bath strain, "MC") as described by Whittenbury et al (J. Gen. Microbiol. 61 (1970) pages 205–218), is grown at 45° C. in batch culture on methane or methanol in ammonium mineral salts medium (Dalton and Whittenbury (1976) Arch. Microbiol. 109, pages 147–151) in a 100 liter fermentor (L.H. Engineering Ltd., Stoke Poges, Bucks, U.K.). The fermentor is inoculated with 10 l. of continuous culture grown previously by the method described by Colby and Dalton (Biochem. J. (1976), 157 pages 495–497), and after further growth for 18 hours, at which time the $E_{540}$ of the culture is about 8 to 15, the product is harvested using a Westfalia continuous centrifuge (Westfalia Separator Ltd., Wolverton, Bucks, U.K.). The centrifuge outflow and fermentor are connected via a stainless steel cooling coil immersed in an ice bath.

The pellet of cells so produced is washed once with ice cold 20 mM-sodium phosphate, or tris HCl buffer, pH 7.0, and resuspended in the same buffer containing 5 mM $MgCl_2$, 5 ml of buffer per liter of culture. Soluble extracts of the cells are prepared by first passing the suspended cell suspension through a French pressure cell at 137 MPa (20,000 lb/inch$^2$) followed by centrifugation by 5000 g for 10 minutes to remove unbroken bacteria. The crude extract is then centrifuged at 80,000 g for 1 h. and the soluble extract remaining is immediately frozen into pellet form by driopwise addition to a Dewar flask containing liquid nitrogen, and the pellets are stored at −70° C. The protein concentration of the soluble extract, as determined with the Folin-Ciocalteu reagent, is found to be 40–80 mg/ml.

EXAMPLE 2

Oxidation of Alkanes

Reaction mixtures are made up to a total liquid volume of 1 ml in 7 ml conical flasks, each mixture containing: 50 μmol of sodium phosphate buffer, pH7; 5 μmol of NADH; 0.5 μmol of KCN, and quantities of alkane substrates, butane, pentane, hexane, heptane and octane. Liquid substrates are incorporated ino the reaction mixtures and gaseous substrates are added to the reaction flasks as a partial replacement for the gaseous phase.

Stoppered flasks are incubated for 4 minutes in a waterbath maintained at 45° C. and reciprocated at 90 oscillations per minute, and oxidation is initiated by injecting freshly thawed soluble extract, as prepared in Example 1, through the stoppers into each flask. 4 mg of extract is added in the case of n-octane, as compared with 2 mg for all other alkanes tested. The rate of oxidation of the alkanes is measured by monitoring the appearance of products.

5 μl samples of the reaction mixtures are injected into a gas chromatograph both immediately after addition of the soluble extract and after 12 mins. incubation, product formation over this period having been found to be more or less linear. In the case of n-octane, however, the products are insoluble and thus the reaction mixture is first extracted with 1 ml of dicholoromethane and a 5 μl sample of the dichloromethane extract is injected into the gas chromatograph. A Pye series 104 flame-ionisation gas chromatograph is used, fitted with 2.1 m glass columns, internal diameter 4 mm, packed with Porapak Q (Waters Associates, Milford, Mass. U.S.A.) with Chromosorb 102 (Johnsmanville, Denver, Colo., U.S.A.) or with 5% (w/w) of Carbowax 20M on 60–80 mesh Chromosorb W. Products are identified by comparing their retention times on each column compared with those of authentic standards, and quantities are estimated from peak height or in some cases peak area. The columns are used in conjunction and operated isothermally at temperatures between 50° and 230° C. with nitrogen gas glow-rates of 15–60 ml/min. All the volatile products observed are positively identified.

The specific activities of the soluble extract in relation to the various alkanes are calculated from the total product formation after 12 minutes incubation, and the results obtained are given in Table 1, which also includes information relating to the quantities of substrates used and products formed.

TABLE 1

Oxidation of C$_4$-C$_8$ alkanes by soluble extracts of M. capsulatus (Bath)

| Substrate (μ mol per reaction flask) | Products (μ mol formed after 12 mins incubation) | Specific Activity m unit/mg of protein |
|---|---|---|
| butane (134) | butan-1-ol (1.10) butan-2-ol (0.92) | 77(0,5,68,0,0) |
| pentane (150) | pentan-1-ol (0.49) pentan-2-ol (1.26) | 73(0,0,69,0,0) |

TABLE 1-continued

Oxidation of C$_4$-C$_8$ alkanes by soluble extracts of M. capsulatus (Bath)

| Substrate (μ mol per reaction flask) | Products (μ mol formed after 12 mins incubation) | Specific Activity m unit/mg of protein |
|---|---|---|
| hexane (150) | pentan-3-ol (<0.06) hexan-1-ol (0.60) hexan-2-ol (0.36) hexan-3-ol (<0.01) | 40(0,0,39,0,0) |
| heptane (150) | heptan-1-ol (0.14) heptan-2-ol (0.51) heptan-3-ol (<0.01) heptan-4-ol (<0.01) | 27(0,0,27,0,0) |
| octane (300) | octan-1-ol (0.04) octan-2-ol (0.39) octan-3-ol (<0.01) octan-4-ol (<0.01) | 9(0,0,9,0,0) |

The figures in parentheses in the right hand column of Table 1 refer respectively to assays done in the absence of NADH, anaerobically under N$_2$, in the absence of KCN, in the presence of 0.2 ml of ethyne, or with boiled extract, and illustrate the dependance of oxidation upon extract, NADH and oxygen, its resistance to inhibition by KCN and its sensitivity to inhibition by ethyne (ethyne is known to be a specific inhibitor of methane oxidation in the organism M. capsulatus.)

The results show that C$_4$ and C$_5$ alkanes are oxidised at comparable rates, and that thereafter the rate of oxidation declines rapidly. Both 1- and 2-alcohols are readily produced; though in the case of the higher alkanes, there is no production of 3- or 4-alcohols indicating that the enzyme is specific for the oxidation of 1- and 2-alkyl carbon atoms.

EXAMPLE 3

Oxidation of Alkenes

Similarly as in Example 2, alkenes, i.e. ethene, propene, but-1-ene, cis-but-2-ene and trans-but-2-ene are oxidised in the presence of soluble extracts of M.capsulatus (Bath) as prepared in Example 1. Also, as in Example 2, specific activities are calculated from the total product formation after 12 mins. incubation. In addition, however, the identification of products is confirmed by treating reaction mixture with 20 μl of HCl or 5 μl of bromine for 5 mins. at 45° C. followed by gas chromatography to determine whether the products still remained, this procedure being based on that of May and Abbott (J. Biol. Chem (1973) 248 pages 1725–1720). Under these conditions bromine reacts with unsaturated compounds by addition whereas dilute hydrochloric acid catalyses the hydrolysis of epoxides. Thus the epoxyethane, 1,2,-epoxypropane-1,2-epoxybutane, cis-2,3-epoxybutane and trans-2,3-epoxybutane products disappeared from gas chromatograms after treatment with HCl but remained after treatment with bromine; whereas the cis-2-buten-1-ol and the trans-2-buten-1-ol products disappeared after treatment with bromine but remained after HCl treatment, the 2-butanone product remaining after both treatments.

The results obtained are given in Table 2, the figures in parentheses in the right hand column being of similar significance to those in Table 1. Both terminal and internal double bonds are oxidised to epoxides. Trans but-2-ene yields both epoxide and buten-1-ol product indicating that the enzyme attack of internal alkenes takes place both at internal double bonds and terminal methyl groups. It should be noted that trans but-2-ene yields only trans products and cis but-2-ene yields only cis products, indicating that the process proceeds with retention of structural configuration.

TABLE 2

Oxidation of $C_2$-$C_4$ n-alkenes by soluble extracts of *M. capsulatus* (Bath)

| Substrate (μ mol per reaction flask) | Products (μ mol formed after 12 mins incubation) | Specific Activity m units/mg of protein |
|---|---|---|
| ethene (134) | epoxyethane (3.54) | 148(0,13,122,120) |
| propene (134) | 1,2-epoxypropane (2.10) | 83(0,0,83,0,0) |
| but-1-ene (134) | 1,2-epoxybutane (1.19) | 49(0,0,49,0,0) |
| cis-but-2-ene (134) | cis-2, 3-epoxybutane (0.61) cis-2-buten-1-ol (0.57) 2-butanone (0.20) | 57(0,0,51,0,0) |
| trans-but-2-ene (134) | trans-2,3-epoxybutane (0.77) trans-2-buten-1-ol (2.52) | 141(0,0,128,0,0) |

EXAMPLE 4

Oxidation of Cyclic Compounds

The oxidation activity of the soluble extract is assayed for cyclohexane and for some aromatic and heterocyclic compounds by the method as in previous examples, 4 mg of extract protein being used in all cases. Specific activities are calculated from the total amounts of products formed after 12 mins. incubation; excepting pyridine in which case the specific activity is determined by monitoring pyridine disappearance from reaction flasks initially containing 3 μmol of pyridine.

The pyridine N-oxide product is identified by thin layer chromatography of a reaction mixture, initially containing 90 μmol of pyridine, after 12 mins. incubation. The reaction mixtures are extracted with an equal volume of dichloromethane which is then separated and evaporated to dryness. The residues remaining are redissolved in 0.1 ml of dichloromethane and spotted on to chromatograms together with authenticated solutions of pyridine N-oxide in dichloromethane. The chromatograms are developed in either methanol or acetone and the $R_f$ values of the reaction product in each solvent are found to be in close agreement with those of the authentic pyridine N-oxide, thus establishing the nature of the product.

As in Example 3, the identification of the other products is confirmed by treatment of reaction mixtures with bromine or HCl followed by gas chromatography. The product of oxidation of cyclohexane is found to remain after both HCl and bromine treatment; the product of benzene oxidation and products of toluene oxidation disappear after bromine treatment but remain after HCl treatment, and the product of styrene oxidation disappears after HCl but remains after bromine treatment, confirming their identification as cyclohexanol, phenol, benzy alcohol, and cresol and styrene epoxide respectively.

The results obtained are given in Table 3 which is of similar layout and content as the Tables in preceding Examples. The aliphatic and aromatic ring structures of cyclohexane and benzene are oxidised to cyclohexanol and phenol respectively, and toluene is oxidised to a mixture of benzyl alcohol and cresol showing enzyme attack takes place on both methyl group ring substituent and aromatic ring. On the other hand styrene is oxidised to its epoxide alone, there being no oxidation of the aromatic ring.

TABLE 3

Oxidation of alicyclic, aromatic and heterocyclic compounds by soluble extracts of *M. capsulatus* (Bath).

| Substrate (μ mol per reaction flask) | Products (μ mol formed after 12 mins incubation) | Specific Activity (m unit/mg protein) |
|---|---|---|
| Cyclohexane (460) | cyclohexanol (3.0) | 62(0,0,62,0,0) |
| benzene (450) | phenol (3.0) | 62(0,0,62,0,0) |
| toluene (460) | benzyl alcohol (1.5) cresol (1.0) | 53(0,0,52,0,0) |
| styrene (90) | styrene epoxide (2.3) | 47(0,0,37,0,0) |
| pyridine (3,90) | pyridine N-oxide (not determined) | 29(0,4,25,0,0) |

The foregoing examples, examples 1–4, are concerned with the preparation and use in processes of the invention of methane-oxidising enzyme extracts of the Bath strain of *M. capsulatus*. It will be appreciated, however, that similar methods may be used with similar results for preparation and utilisation of methane oxidising enzyme extracts of other methane-oxidising bacteria in general. Specific details of technique and procedure used may vary dependent upon the nature of the organism and its enzyme extract, though these variations will be apparent to workers skilled in the art.

EXAMPLE 5

Oxidation of Propene by Whole Organisms of Various Methane-Oxidising Bacteria In a modification of the procedure adopted in Examples 2–4, propene is oxidised by whole organisms of various methane-oxidising bacteria, namely *M. capsulatus* (Bath), *Methylomonas albus* (BG 8), *Methylomonas agile* (A 20), *Methylocystis parvum* (OBBP), *Methylosinus trichosporium* (OB3b) and *Methylomonas methanica* (PM).

Cultures of the various organisms are grown in a chemostat at a dilution rate of 0.07 hr$^{-1}$, harvested by centrifugation and resuspended in 20 mM phosphate buffer, pH 7. A 1 ml aliquot of suspension containing the equivalent of 0.8 mg dry weight of each bacterium is placed in a 7 ml conical flask together with 4 μmol of formaldehyde as electron donor, and 2 ml of propene gas is injected into each flask.

The specific activity for oxidation of propene to 1,2-epoxypropane by whole organisms is determined as in previous examples, and the results obtained for the various organisms are given below in tabular form.

TABLE 4

Oxidation of propene by whole organisms

| Organism | Activity (m units per mg cell protein) |
|---|---|
| "*Methylococcus capsulatus*" (Bath) | 45 |
| "*Methylomonas albus*" (BG 8) | 100 |
| "*Methylomonas agile*" (A 20) | 80 |
| "*Methylocystis parvum*" (OBBP) | 35 |
| "*Methylosinus trichosporium*" (OB3b) | 70 |
| "*Methylomonas methanica*" (PM) | 80 |

EXAMPLE 6

Use of Formate as substitute for NADH as Electron Donor

In modification of Examples 2–4 formate together with a catalytic quantity of NAD$^+$ is used as a substitute for the NADH required to drive the reaction of the enzyme extract.

Flasks are set up as indicated in Examples 2, 3 and 4, except that NADH is omitted and replaced by 0.1 µmol NAD+ and 5 µmoles of potassium formate. Endogenous levels of formate dehydrogenase (EC 1.2.1.2; 280 m units per mg extract protein) catalyse the formation of NADH from NAD+. This system is as effective as using NADH alone in the catalytic oxidation of the substrates of Examples 2, 3 and 4.

As a further alternative the catalytic amount of NAD+ required is immobilised on a support, such as Sepharose, Agarose or dextran and the immobilised material is recovered after use. Examples of other electron donors which are used to replace potassium formate include formaldehyde, glucose-6-phosphate, 6-phospho-gluconate, sodium isocitrate, and possibly ethanol. (In this latter case the enzyme extract may be fortified with a suitable preparation of alcohol dehydrogenase e.g. a crude extract of yeast.)

We claim:

1. A process for oxidizing an alkene comprising: contacting said alkene with a culture of methane-oxidizing *Methylococcus capsulatus* (Bath) bacteria or an extract of said culture which contains a methane-oxidizing enzyme system under conditions of medium and temperature, and for a period of time required for, oxidation of said alkene.

2. A process for oxidizing propene comprising: contacting said propene with a culture of methane-oxidizing bacteria selected from the group consisting of *Methylmonas albus* (BG8), *Methylmonas agile* (A20), *Methylcystis parvum* (OBBP), *Methylosinus trichosporium* (OB3b), *Methylomonas methanica* (PM) and mixtures thereof or an extract of said culture which contains a methane-oxidizing enzyme system under conditions of medium and temperature, and for a period of time required for, oxidation of said propene.

3. A process for oxidizing an organic compound, selected from the group consisting of cyclohexane, benzene, toluene, styrene, pyridine and mixtures thereof, comprising: contacting said organic compound with a culture of methane-oxidizing *Methylococcus capsulatus* (Bath) bacteria or an extract of said culture which contains a methane-oxidizing enzyme system under conditions of medium and temperature, and for a period of time required for, oxidation of said organic compound.

4. The process of claim 1, wherein said alkene is selected from the group consisting of ethylene, propene, butenes and mixtures thereof.

5. The process of claim 1; wherein said extract is employed, and in which a co-factor or other biochemical species required to drive said oxidation is regenerated.

6. The process of claim 2, wherein said extract is employed, and in which a co-factor or other biochemical species required to drive said oxidation reaction is regenerated.

7. The process of claim 3, wherein said extract is employed, and in which a co-factor or other biochemical species required to drive said oxidation reaction is regenerated.

8. The process of claim 5, wherein said regeneration is achieved by interaction of an electron donor with a catalytic amount of said biochemical species after oxidation.

9. The process of claim 8, wherein said electron donor is formaldehyde or formate.

10. The process of claim 6, wherein said regeneration is achieved by interaction of an electron donor with a catalytic amount of said biochemical species after oxidation.

11. The process of claim 10, wherein said electron donor is formaldehyde or formate.

12. The process of claim 7, wherein said regeneration is achieved by interaction of an electron donor with a catalytic amount of said biochemical species after oxidation.

13. The process of claim 12, wherein said electron donor is formaldehyde or formate.

14. The process of claim 1, wherein propene is oxidized to 1,2-epoxy propane.

* * * * *